(12) United States Patent
Heidenreich et al.

(10) Patent No.: US 9,721,118 B2
(45) Date of Patent: Aug. 1, 2017

(54) SECURING ACCESS TO DISTRIBUTED DATA IN AN UNSECURE DATA NETWORK

(75) Inventors: Georg Heidenreich, Erlangen (DE); Wolfgang Leetz, Uttenreuth (DE)

(73) Assignee: SIEMENS AKTIENGESELLSCHAT, Munich (DE)

(*) Notice: Subject to any disclaimer, the term of this patent is extended or adjusted under 35 U.S.C. 154(b) by 549 days.

(21) Appl. No.: 13/982,574

(22) PCT Filed: Jan. 24, 2012

(86) PCT No.: PCT/EP2012/051047
§ 371 (c)(1),
(2), (4) Date: Jul. 30, 2013

(87) PCT Pub. No.: WO2012/107275
PCT Pub. Date: Aug. 16, 2012

(65) Prior Publication Data
US 2013/0318626 A1 Nov. 28, 2013

(30) Foreign Application Priority Data
Feb. 8, 2011 (DE) .................. 10 2011 003 784

(51) Int. Cl.
G06F 21/62 (2013.01)
G06F 19/00 (2011.01)
(Continued)

(52) U.S. Cl.
CPC ...... *G06F 21/6245* (2013.01); *G06F 17/3056* (2013.01); *G06F 19/322* (2013.01); *G06F 21/6254* (2013.01); *H04L 63/0421* (2013.01)

(58) Field of Classification Search
CPC ............ G06F 21/6245; G06F 21/6254; G06F 17/3056; G06F 17/30; G06F 19/322;
(Continued)

(56) References Cited

U.S. PATENT DOCUMENTS 5,944,824 A * 8/1999 He .......................... G06F 21/33
726/6
2004/0078587 A1 4/2004 Brackett et al.
(Continued)

FOREIGN PATENT DOCUMENTS

CN 101674304 A 3/2010
EP 1416419 A2 5/2004
(Continued)

OTHER PUBLICATIONS

Chinese Office Action and English translation thereof dated May 5, 2015.
(Continued)

Primary Examiner — Eleni Shiferaw
Assistant Examiner — Nelson Giddins
(74) Attorney, Agent, or Firm — Harness, Dickey & Pierce, P.L.C.

(57) ABSTRACT

A method, a system, a registry, a repository and a computer program product are disclosed for securely accessing sensitive medical data records stored in a repository. Before accessing security-critical data in the repository, a registration inquiry with a separate registry must be carried out in order to obtain a security token having limited temporary validity, for example in the form of a barcode. A data source and/or a data sink can then use the security token to access the security-critical data in that an index module indexes the data record inquired about on the repository.

15 Claims, 2 Drawing Sheets

(51) Int. Cl.
  *G06F 17/30* (2006.01)
  *H04L 29/06* (2006.01)
(58) Field of Classification Search
  CPC ... G06F 19/32; G06F 19/321; H04L 63/0421;
  G06Q 50/22; G06Q 50/24
  See application file for complete search history.

(56) References Cited

U.S. PATENT DOCUMENTS

| | | | | |
|---|---|---|---|---|
| 2004/0088355 | A1* | 5/2004 | Hagan | G06F 21/6254 709/203 |
| 2004/0215981 | A1* | 10/2004 | Ricciardi | G06Q 10/10 726/27 |
| 2005/0236474 | A1 | 10/2005 | Albertson et al. | |
| 2005/0283620 | A1 | 12/2005 | Khulusi | |
| 2007/0075135 | A1* | 4/2007 | Dettinger et al. | 235/382.5 |
| 2007/0192134 | A1* | 8/2007 | Littenberg et al. | 705/2 |
| 2007/0245144 | A1* | 10/2007 | Wilson | 713/170 |
| 2008/0235780 | A1* | 9/2008 | Olive | G06F 21/6245 726/9 |
| 2008/0304663 | A1* | 12/2008 | Canard | G06F 21/6254 380/45 |
| 2009/0206992 | A1* | 8/2009 | Giobbi | G06F 19/322 340/5.74 |
| 2010/0328320 | A1* | 12/2010 | Kerstna | A61N 1/37282 345/501 |
| 2011/0112970 | A1* | 5/2011 | Yu | G06F 21/6254 705/51 |
| 2012/0059668 | A1* | 3/2012 | Baldock et al. | 705/3 |

FOREIGN PATENT DOCUMENTS

| | | |
|---|---|---|
| WO | WO 2005088899 A1 | 9/2005 |
| WO | WO 2009083922 A1 | 7/2009 |
| WO | WO 2011002905 A2 | 1/2011 |

OTHER PUBLICATIONS

International Search Report PCT/ISA/210 for International Application No. PCT/EP2012/051047 Dated Jan. 24, 2012.
International Written Opinion PCT/ISA/237 for International Application No. PCT/EP2012/051047 Dated Jan. 24, 2012.
German Office Action 10-2011-003-784.5 Dated Nov. 2, 2011.

* cited by examiner

SECURING ACCESS TO DISTRIBUTED DATA IN AN UNSECURE DATA NETWORK

PRIORITY STATEMENT

This application is the national phase under 35 U.S.C. §371 of PCT International Application No. PCT/EP2012/051047 which has an International filing date of Jan. 24, 2012, which designated the United States of America and which claims priority to German patent application number DE 10 2011 003 784.5 filed Feb. 8, 2011, the entire contents of each of which are hereby incorporated herein by reference.

FIELD

At least one embodiment of the present invention generally relates to security technology and in particular to the access protection of security-critical data records in an unprotected network of distributed databases, such as e.g. a cloud system. At least one embodiment of the invention further generally relates to the field of medical engineering technology which is characterized in particular by a need to store and provide security-critical data.

In the context of modern systems in particular, provision is made for data storage to be configured as flexibly as possible, such that the data can be retrieved and stored by different systems and in particular such that communication via the internet is also possible.

BACKGROUND

Particularly in the field of medical engineering technology, it is therefore an essential requirement to protect the access to security-critical data against unauthorized access. In modern systems which allow access via the internet, this represents a significant source of risk. Unauthorized users can illegally listen in to messages between the individual electronic modules (transmitters, receivers), and this can usually be achieved without great effort or expense. On one hand the access to this data must therefore satisfy strict security requirements. On the other hand the system must be as flexible as possible, allowing use with the web and access from e.g. remote medical workstations, and it must be possible for individual electronic entities to be connected up to the system at any time. In addition, a large group of users, applications and distributed databases must be managed. The large volume of data to be stored must also be taken into consideration when designing security systems.

Protection of electronic data records against unauthorized access is disclosed in the prior art. Encryption systems are known which can be applied both to the storage (e.g. to the hard disks of the computer) and to the communication between the network users. In the context of encryption systems, in which the communications (i.e. the exchanged messages) are encrypted, it is known in the prior art to perform the decryption on the receiver side in each case. This represents a security risk to the extent that it is essentially possible for an unauthorized user to intercept the message (albeit in encrypted format) and process it in some way in an unauthorized manner, corrupt it or forward it without authorization. The prior art also discloses the provision of indices for searching, in order to allow access to data records within a large data resource. However, no provision is made for an approach whereby security-critical personal data can be secured.

SUMMARY

At least one embodiment of the present invention provides an information technology system which secures the access to security-critical data communicated in an unprotected network and at the same time allows indexing with a high-speed search function. Furthermore, in at least one embodiment, provision is made for the data access to security-critical data, particularly medical data records of a patient, to be organized more flexibly while complying with the most stringent security requirements.

It is also aimed, in at least one embodiment, to provide an information technology infrastructure which allows cost savings insofar as the previously required local protection of hard disks in the individual systems can be replaced by a central protection system.

A method, a system, a registry, a repository and a computer program product are disclosed.

The invention is described below with reference to its embodiment as a method. Advantages, alternative embodiment variants or advantageous developments cited in this context can also be applied to the other claims/embodiments likewise, in particular to the system, the registry, the repository and/or the computer program product, and vice versa. In other words, the system (or the other subject matter claimed) can also be developed by features that are described and/or claimed in the context of the method. According to a preferred embodiment, the method is a computer-implemented method. However, alternatives make provision here for at least partial use of a hardware solution, such that the individual steps of the method are executed by corresponding hardware modules having the corresponding functionality, e.g. as components of a microcontroller or microprocessor. In principle, all of the steps of the method need not be executed on the same computer entity in this case, and the method can instead be embodied for a distributed system such that individual steps are executed on a first computer entity and the other steps are executed on further computer entities.

One aspect of an embodiment of the invention therefore relates to a computer-implemented or microprocessor-implemented method for secure access to data records in an insecure network environment such as the internet, for example. In this case provision is made for the interaction of different hardware entities, which are completely isolated from one another and therefore separate in a physical sense:

a central registry, which is embodied as a computer entity for access registration;
  at least one repository, which is provided separately from the registry and is intended for the data storage of security-critical data; and
  at least one data source and at least one data sink.

The data source and the data sink execute accesses to the data records of the registry and/or repository. It is preferably provided that the data source or the data sink must register once with the registry in order to execute an access.

As mentioned above, the preferred embodiment relates to a use in the field of medical engineering technology, and therefore the data records represent security-critical (patient) data. The data records also include demographic data, such as e.g. the patient name, the patient date of birth, the patient location, insurance data, etc., which normally has less strict security requirements for access than the security-critical data (e.g. anamnesis data, findings data, medical images).

Simply stated, it can be taken as a starting point that embodiments of the inventive proposal comprise four separate computer entities: a registry, a repository, a data source (e.g. a medical imaging system or an image storage system) and a data sink (e.g. a findings evaluation workstation). Of course, it is likewise within the scope of the invention to make provision here for a plurality of the entities cited above, such that e.g. a multiplicity of repositories interact with a multiplicity of data sources and a multiplicity of data sinks, which communicate via a communication network in each case. For ease of understanding, the following description generally refers to only one of the above-cited entities, though the invention is not limited thereto.

It is considered an essential aspect of an embodiment of the present invention that a person's security-critical data is never communicated via the network (e.g. the internet as an unsecured network environment) in a shared message with—i.e. never together with—data that identifies a person. This approach has the essential advantage that even if unauthorized users listen in to the data traffic and ascertain data, they will not be able to associate this with a person. Therefore an association between person and security-critical data is impossible even if messages are intercepted.

According to an embodiment of the invention, the method comprises method steps as follows:

the security-critical data and the demographic data are provided separately in that the demographic data is stored in the registry and the security-critical data is stored in the repository;

a registration inquiry is sent from the data source and/or the data sink to the registry in order to obtain a registration in the form of an allocation of a security token for access to a data record that is associated with a person;

in response to this registration inquiry, a security token which can be uniquely associated with a person-identifying data record is issued to the inquiring data source and/or data sink by the registry;

a message is sent from the registry to the repository, comprising the security token that has been issued and the associated person-identifying data record, wherein said message can be used as a basis for a mapping rule that will be executed (possibly at a later time) on the repository;

an access message containing the security token or an identification code that is unique to the inquiry is sent from the data source and/or the data sink to the repository in order to access security-critical data which is stored in the repository, wherein either the security token or a unique identification code, which itself has a one-to-one association with the security token, can be sent;

the mapping rule is applied on the repository using the security token of the access message in order to derive the person-identifying data record, wherein the person-identifying data record is then to be inventively used as an index for addressing the data record of security-critical data that is requested by the access;

the access to the (requested) data record is performed using the person-identifying data record as an index.

The terminology used within the context of this patent application is explained below.

The data records comprise at least two data parts: one part contains "security-critical data", requiring the maximum level of protection measures (highest security requirements); and one part contains demographic data, requiring lesser protection measures and hence a lower degree of sensitivity. The primary application of the method according to the invention is in the field of medical engineering technology. Security-critical data here comprises e.g. health data relating to a patient, such as findings data, medical image data, anamnesis data, report data, etc. However, in alternative embodiments applications may also include financial applications, insurance applications, or any other applications which involve the processing of security-critical data. The "demographic data" is referred to as "public data" in the specialist literature, since it is already published on mobile data media (e.g. in the form of an insurance card (or the planned healthcare card): family name, date of birth, etc.). The term "unsecured network environment" is intended to signify any cloud systems or network systems in which the computer-based entities exchange data. As soon as a network is open to an arbitrary number of subscribers for the purpose of data transfer, it is "unsecured" within the meaning of the invention. This applies not only to the internet, but also to wide area networks (WANs) or local area networks (LANs), e.g. corporate networks, hospital networks or groups of associated networks, or to other digital networks.

The terms "registry" and "repository" are intended to signify computer-based, physical hardware entities, which comprise external or internal hard disks (e.g. RAID systems) or other methods/systems of data storage and interfaces for communicating with other entities. They are also intended for storing mapping rules for the purpose of indexing data records which are held in their storage. Both the data records stored in the registry and those stored in the repository can be addressed and/or indexed via an index.

The "identifier" is preferably a person-identifying data record. In respect of its use in the context of medical engineering technology, it clearly must be the case that both the demographic data records (of a patient) and the security-critical data records (of a patient) must only be associated with precisely one patient. A one-to-one association between identifier and person (as a patient) must be possible. The system preferably provides a bijective mapping for this purpose. Errors occur if an identifier is associated with different people or if different identifiers are associated with one person. The latter is disclosed in the prior art as a problem of duplicates. Both eventualities must be avoided.

According to an embodiment of the inventive solution, the identifier is preferably generated by the system itself, and can be formed in accordance with local security precautions. A combination of demographic data is generally used here, possibly in conjunction with further identifying information (optionally supplemented further by specifying an electronic address of the computer-based entities involved, a timestamp or a random number, or further parameters). However, it is alternatively also possible for the external systems, i.e. the data source and/or the data sink, to provide and use their own identifier. This need not necessarily correspond to the identifier of the system. An association is then made between data source/data sink ID and internal ID. Any duplicates that may be present can be combined in the registry by virtue of this association.

The demographic data is stored in the registry. Also stored is an association (preferably in the form of a tabular data structure):

person-identifying identifier < > demographic data.

Since the security tokens are preferably not used more than once, the invention makes no provision for these to be stored, since this would represent a security risk. Although the association "security token < > identifier" must be available, it must not be stored.

The security-critical data is stored in the repository. In addition to this, the repository also includes two associations (again preferably in the form of tabular data structures):

1. association between person-identifying identifier < > security-critical data record; and
2. association between security token < > person-identifying identifier.

As mentioned above, it is provided according to an embodiment of the invention that the person-identifying identifier should preferably be generated by the internal system which manages the registry. In this way the repository merely uses the identifiers that are transferred by the registry with the security token.

The term "data source" signifies computer-based entities which generate data records and transfer them to the repository for storage, such that they are accessible to other entities there. The data sources can be computers, computer networks, devices (e.g. laboratory devices), imaging medical systems, etc. They preferably communicate via a specific protocol, in particular the DICOM protocol (DICOM: Digital Imaging and Communications in Medicine).

The "data sink" likewise relates to computer-based entities which function in the manner of clients and request data from the repository. They include workstations, mobile devices (PDAs, laptops, etc.) or other electronic modules in this case. The access system according to an embodiment of the invention preferably comprises a central registry, a multiplicity of repositories, a multiplicity of data sources and a multiplicity of data sinks. Alternatively, other embodiments are also conceivable here, such that a plurality of registries may be provided and managed by a supervisory entity, for example. Likewise, provision may be made for only one repository, which then functions as a central store. It is an essential feature of the invention that all of the participating entities are spatially or physically separate and interact with one another via an open network (e.g. via the Internet).

The "security token" is preferably a digital pseudonym. This means that a unique association exists between a person-identifying data record and the pseudonym. In respect of the generation of the pseudonym, it must not be possible to infer person-related data records from the pseudonym. In other words, an unauthorized user who "listens in" to the pseudonym cannot deduce anything about the person or data records (security-critical or demographic data) that are stored for the person. In an alternative embodiment, the security token can also be developed as a hardware feature and take the form of a security feature (hardware component with integrated security chip, etc.), for example.

It is considered an essential advantage of an embodiment of the inventive solution that the system can also be adapted flexibly to further requirements during operation of an embodiment of the inventive method. For example, repositories, data sources and/or data sinks can also be changed (for example added, removed or modified) during operation. The system can therefore be adapted to the current requirements and is therefore scalable.

According to an example embodiment, provision is made for the communication protocol for communication between the participating entities to be asynchronous. This (is very widespread in practice and) has the advantage that messages exchanged between the participating entities can be answered at any time. However, use of a synchronous communication protocol or a mixture of asynchronous and synchronous protocols also lies within the scope of the invention.

The pseudonym or the security token is preferably generated by the system. In an example embodiment this takes place directly on the registry. Alternatively, the pseudonym can also be generated on other computer-based entities (e.g. using a random generator) and then transferred to the registry via an interface. It is essential that the data source sends an inquiry with an identifier to the registry for the purpose of registration. The identifier can be an identifier that was generated by the data source and identifies the data records in the data source in this case. Alternatively, the identifier can also be a system-internal identifier which identifies the data records in the registry/repository. In response to the inquiry with the identifier from the data source, the registry generates the relevant pseudonym (the security token) and therefore associates an identifier uniquely with a pseudonym. The registry then sends the pseudonym to the inquiring data source as a reply to the inquiry.

The same method applies in respect of an inquiry from the data sink. In this case the data sink sends a registration inquiry with an identifier to the registry. The latter generates the security token for the identifier and associates it with the identifier (internally within the system). The registry then sends the pseudonym (the security token) to the inquiring data sink as a reply to the inquiry.

In both of the cases cited above (registration inquiry from the data source and registration inquiry from the data sink), the registry can respond in two different ways:
1. The registry sends back only the security token as a reply in each case. The inquiring entity (data source/data sink) then associates the received security token with the respective identifier on the basis of the sequence of the messages concerned; or
2. the registry sends back not only the security token as a reply, but also the respective identifier that is associated with the security token (or the respective identifier that is associated with the inquiry) in addition to the security token. The identifier < > security token association is unique in this case, i.e. infective in a mathematical sense. According to the invention, for reasons of security, the same token is not used for a subsequent further inquiry. Therefore the inquiring entity (data source/data sink) does not have to undertake any management in respect of the messages and can extract the association between identifier and security token directly from the reply of the registry.

Once the registry has created the association between identifier and security token and replied to the inquiring entity, the registry sends a message to the repository in order to inform the repository likewise of the association between identifier and security token.

In an example embodiment, provision is made for the security token to have only temporary validity and therefore to expire automatically after a configurable time period. After expiry of this time period, access to data is no longer possible using the security token. The validity of the security token is managed by the repository. Alternatively, it is also possible to manage the security token from the registry and send corresponding messages to the repository.

Following execution of the steps cited above, both the inquiring entity (data source or data sink) and the repository are informed of the currently allocated security token.

Consequently, the inquiring entity (data source, data sink) is able to send an access inquiry to the repository as it is registered for access (specifically by virtue of possessing a security token). The data source/data sink sends an access message comprising the security token to the repository.

In a next step, the repository can uniquely infer the identifier from the received security token and from the mapping rule that was received from the registry (association between identifier and security token). This is preferably done by accessing a table.

In a further step, a further table in the repository can then be accessed. The identifier that was derived in the first step is used for this purpose, in order to indicate the required data record of security-critical data by means of the identifier. In other words, the derived identifier is used as an index for the access to the required security-critical data record. In the following step, this data record can then be changed according to the type of access.

If the access was executed by the data source, a write access is provided and therefore the data source sends the "new" security-critical data to the repository in order to store it there under the identifier or to overwrite or modify the identified security-critical data record correspondingly.

If the inquiring entity was the data sink, a read access is required. In this case the indexed security-critical data record from the repository is sent to the data sink as a reply to the access inquiry (access message). Two variants of this are provided according to an embodiment of the invention:

1. In response to an inquiry from the data sink in respect of a read access, the repository can reply by sending the indexed data record of security-critical data to the data sink. In this case the data sink receives solely the data record as a reply to its read inquiry. The management of the received messages and in particular of the data records is the responsibility of the data sink in this case. On the basis of the message that is received from the repository and contains the requested security-critical data, the data sink must find an association with the identifier. This can be achieved using the sequence of the exchanged messages and/or a corresponding timestamp.
2. In response to an inquiry from the data sink for a read access to security-critical data, the repository replies by transferring not only a message containing the requested security-critical data, but a combination (optionally an alternative combination of possibly different message formats, e.g. via digital and postal devices), preferably in the form of an ordered set, comprising: the requested security-critical data and the security token associated with this data (or an identifier associated with the inquiry). In this case the data sink does not have to execute any further management steps, but can directly infer the association between identifier and security-critical data on the basis of the reply message received from the repository.

One advantage of the first variant of an embodiment is that the security can be increased even further, since the security-critical data from the repository to the data sink is only ever transferred on its own and without a further security token (which indirectly allows the person to be inferred).

Alternatively, the repository can send two messages as a reply to a read access from the data sink: the one being a message comprising the requested security-critical data and the other, second message, which can temporally precede or succeed the first, in the form of the associated security token in each case. The management overhead on the data sink is eliminated in this embodiment. The security level can nonetheless be increased, since the security-critical data is used without any further addition.

These embodiments also exist for the write access from the data source to the repository:

1. The data source sends two different messages to the repository, these being staggered in time or in different data formats, for example. In a first message, it sends the security token that is used by the repository to index the respective data record. In a second message, it sends the respective security-critical data for the write access. The repository indexes the data thus received using the previously received identifier which is derived from the security token.
2. In a second variant, the data source does not send two separate messages, but only one message comprising both the security token and the security-critical data. The repository again uses the security token to index the security-critical data.

The security-critical data is preferably stored directly on the repository. Alternatively it is provided for the repository just to hold pointers (links) to the security-critical data, which is stored on another entity. Data is exchanged between the repository and the further entity in this case.

By virtue of the asynchronous protocol, a data source may be executing a write access to the repository while the data sink is requesting or executing a read access to another data record in the repository at the same time. Moreover, execution of the method steps for registering the inquiring entity (data source, data sink) may be temporally independent of the respective data access of the inquiring entity to the repository. In this case it is necessary merely to consider the temporal validity period of the security token. Provided this validity period is complied with, the registration process can be performed at any time before the execution of the access. The method can therefore be configured even more flexibly.

It is an essential advantage of an embodiment of the inventive solution that access to the security-critical data in the repository can be executed far more quickly, since direct indexing using the unique identifier is possible. The data records stored in the repository can therefore be addressed selectively, not only within the repository but also by the inquiring entities, namely the data source and the data sink.

Furthermore, the security of the access system is significantly increased since only messages are exchanged by different entities, as mentioned above, and person-specific data records are never used together with security-critical data in a message. In other words, the participating physical entities (data source, data sink, registry and repository) are so far apart that even an unsecured network such as the internet can be used to exchange security-critical data, wherein the data is also protected to the greatest extent possible against unauthorized access, even if the messages are monitored.

It is also an essential advantage that the access can be significantly accelerated because the individual hard disks of the repository do not need to provide the same degree of access protection as was previously necessary, and the access is therefore essentially accelerated since the security-critical data is inventively not communicated with person-identifying information.

It is also considered an essential aspect of an embodiment of the invention that use is made of two different identification features: one being the person-identifying identifier that applies to a person and is valid throughout their life, the other being the security token which is generated by the system and has only temporary validity. It must be impossible for a third party to infer the security token from the identifier. Likewise, a third party must be unable conversely to infer the identifier from the security token. An identifier should essentially identify a person on a one-to-one basis. In other words, provision is made for a bijective mapping between real person and identifier. However, so-called duplicates are tolerated in existing IT health systems for security reasons. In principle, a person can therefore have different identifiers.

According to an embodiment of the invention, the repository can always resolve these duplicates with reference to external demographic features, and perform multiple iterations of the above-described process for transferring security tokens accordingly. This resolution can be introduced, modified or disabled as a method in the registry at any time, without changing permanent data resources.

The identifier is normally generated by the registry. Various mechanisms can be provided for this purpose. A hash function is usually executed on a combination of different parameters comprising all or a selection of the following data: demographic data, local time data, possibly a region code that is unique to the network, and possibly further parameters. Alternatively, the identifier may be generated not by the registry but by another entity, e.g. the inquiring entity (data source, data sink) or other entities, then forwarded to the registry. In any case it must be ensured that a third party cannot use the knowledge of one security token to infer another security token.

It should be noted in this context that the mechanisms for generating the security token do not restrict the subject matter of an embodiment of the present invention. In other words, different methods of token generation are also possible. For example, a hash function could be applied to the following parameters: a GUID (globally unique identifier) which is generated by the operating system platform upon request, the local time, a random number and/or the expiry time of the validity of the new security token.

A system for secure access to data records is further disclosed in an embodiment. The system comprises hardware entities which are physically separate from one another: preferably a central registry, at least one repository, a multiplicity of data sources and a multiplicity of data sinks.

According to an embodiment of the invention, the registry is so extended as to include a notification module which is embodied to send a message from the registry to the repository in order to inform the repository of the security tokens that are currently issued for the associated identifiers in each case.

According to an embodiment of the invention, the data source is so embodied as to include a registration module for the purpose of sending a registration inquiry to the registry and receiving the result (containing the security token). In addition, the data source is so embodied as to include an access module for the purpose of executing a write access to the repository using security-critical data and the security token.

The data sink is likewise so embodied as to include a registration module for the purpose of sending the registration inquiry to the registry and receiving the result (security token). In addition, the data sink is so embodied as to include an access module for the purpose of executing the read access from the data sink to data records in the repository. It is used to send a read access with the security token to the repository and to receive the reply from the repository, comprising the requested security-critical data which is associated with the security token.

According to an embodiment of the invention, the repository is so developed as to include an index module which is embodied to access two tables in order to derive an identifier from the security token of the inquiring entity and, in a second step, to index the requested security-critical data record from the derived identifier and prepare it for the access.

The alternative embodiments of the invention described above in connection with the method can likewise be applied to the system comprising the modules.

An embodiment of a registry and a repository are disclosed, as well as a computer program product. The computer program product of an embodiment can comprise a computer program which may be stored on a storage medium (e.g. a portable data storage medium or an internal storage medium of a computer). The computer program can also be provided as a distributed system, such that individual modules, these being defined by the individual functions of the method steps, are executed on the various entities of the system. Individual parts of the computer program can be made available for downloading in this case.

BRIEF DESCRIPTION OF THE DRAWINGS

Without thereby limiting the scope of the invention, the following detailed description of the figures describes example embodiments and their features and further advantages with reference to the drawing, in which.

DETAILED DESCRIPTION OF THE EXAMPLE EMBODIMENTS

The invention is explained in greater detail below in connection with an example embodiment and with reference to FIG. 1.

Embodiments of the invention relate to a system and a method for secure access to data records in an unsecured network environment such as the internet, for example. Data is exchanged via the internet by participating hardware entities such as storage entities comprising a multiplicity of hard disks, a multiplicity of data sources Q which make data available (and whose contents differ as a function of the application), and a multiplicity of data sinks S that request data.

Figure 2:
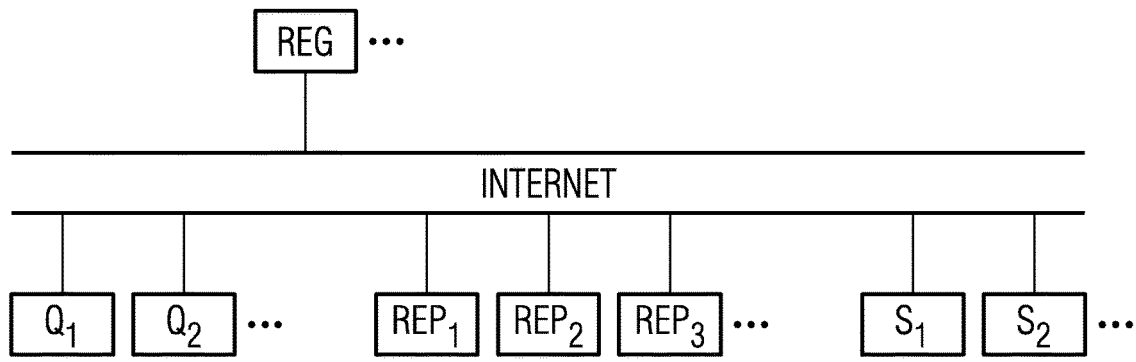
FIG. 2 shows a schematic representation of participating physical entities in a general illustration.

As shown schematically in FIG. 2, in an example embodiment of the invention a central registry REG is provided which communicates via the internet with further hardware entities: with a multiplicity of data sources Q1, Q2; a multiplicity of repositories REP1, REP2, REP3; and a multiplicity of data sinks S1, S2, etc. Alternatively, it is also possible to provide not just one central registry REG, but a plurality of registry entities which are managed by a supervisory entity. It is then necessary to address the correct registry when data is exchanged. The other entities comprising data source Q, repository REP and data sink S exchange data via the internet.

Figure 1:
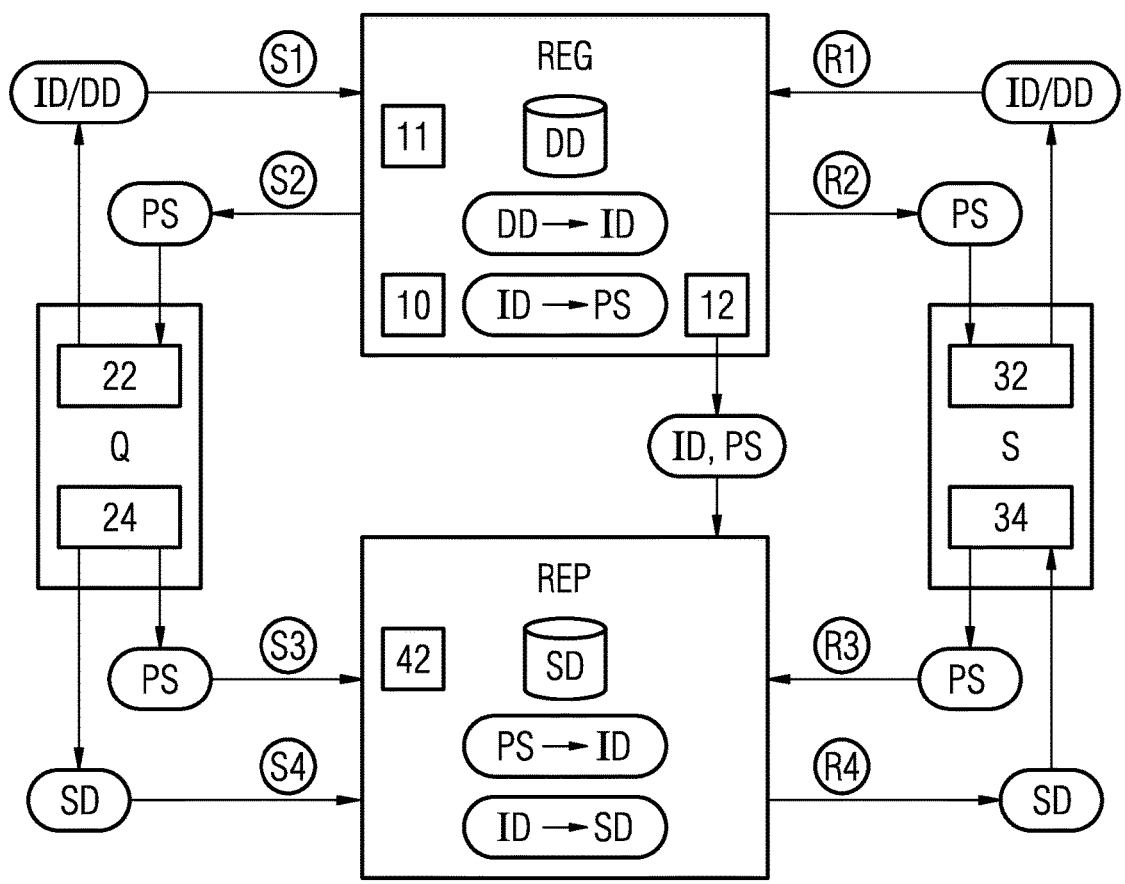
FIG. 1 shows a schematic overview of an inventive system according to an example embodiment, with exchanges of messages and their chronological sequence.

For the sake of clarity and simplicity, only one data source Q, one repository REP and one data sink S are illustrated in FIG. 1 in order to explain the exchange of data between these entities. As mentioned above, a multiplicity of data sources Q, repositories REP and data sinks S are provided in reality.

In a principal embodiment of the invention, the method relates to provision of secure access to medical or health-related data records via the internet. The data sources Q are medical imaging systems and archiving systems such as e.g. PACS (Picture Archiving and Communication System) systems, which are themselves normally implemented as a network and access a cloud of repositories REP. Of course, the data sources Q may also have local storage at their disposal. The data sources Q can essentially be embodied in the form of different hardware-based or computer-based entities which can be used to perform the function of data provider (supplier) or transmitter in the respective application. The data sinks S may be, for example, any chosen clients working at workstations in order to view medical findings or otherwise process patient data, for example. Depending on the application, the data sinks may comprise different computer-based components which request data as part of their function.

An embodiment of the present invention derives from the fundamental problem of how security-critical data (e.g. medical patient data or other financial user data requiring protection) can be transferred quickly and securely in a network, wherein access from all participating entities to the relevant security-critical data should at the same time be as flexible as possible. For today's applications, access via the internet can provide the greatest flexibility. However, the exchange of data via the internet is highly insecure, since third parties can listen in to the data and misuse of the intercepted data is therefore possible. Consequently, the two objectives cited above are actually inconsistent and dichotomous or complementary. Faced with the problem of making the data exchange more secure, a person skilled in the art does not generally think of using the unprotected internet. The solution according to an embodiment of the invention nonetheless proposes a system in which the internet can be used, but in which the exchange of data between the participating entities via the internet meets the strictest security requirements inasmuch as messages are never exchanged which communicate person-identifying data together with security-critical data.

The proposed system and/or method for access essentially relates to sensitive data and/or data having different security levels. Depending on the application, this may be health data relating to a patient or financial data of a user, for example. In this case provision is made for dividing these data records into two different categories:

1. demographic data DD; and
2. security-critical data SD.

The demographic data is likewise security-critical data, but is slightly less sensitive than the security-critical data SD. Demographic data DD comprises e.g. the name, the place of birth, the date of birth, the insurer, the employer of the person concerned or identities that are issued by an external entity (not associated with the registry REG and not associated with the repository REP). The "external identities" can be for example an external identifier such as e.g. an index that is used by the data source and/or by the data sink to address the data records on the data source/data sink. This identifier does not necessarily have to correspond to the identifier that is used by the registry/repository system. A mapping is provided for this purpose according to an embodiment of the invention.

It is an essential feature of the invention that the demographic data DD and the security-critical data SD are provided in two different hardware entities (e.g. storage servers) and are physically separate from one another. The demographic data DD is provided in the registry REG and the security-critical data SD is provided in the repository REP.

If access to the security-critical data SD in the repository REP is requested from any location, this is only possible if, in a first step, a registration could be successfully requested from the registry REG and provided to the relevant inquiring entity first.

Sensitive data is stored in both the registry REG and the repository REP. These data records must be addressable for the purpose of access.

According to an embodiment of the invention, provision is now made for two different identification systems to be used for the purpose of addressing the respective data records:

1. a person-identifying identifier ID; and
2. a security token, which can also take the form of a pseudonym PS.

The (internal) identifier ID is used to identify a person, and hence a data record which is associated with this person on a one-to-one basis. For example, the identifier ID can be used to address all of the findings files, all the image data, and the demographic data DD of the patient. The identifier ID indexes the person-specific data records in the system of the registry REG and the repository REP. It should be noted in this case that both the data source Q and the data sink S can have different identifiers.

For the purpose of security it is provided that the identifier ID is only used internally and is not included in any message to data source Q or data sink S (and is therefore not sent externally); only the registry REG transfers a message containing the identifier ID to the repository REP. The communication between these two entities is preferably subjected to stricter monitoring (e.g. encryption, etc.). The security token or the pseudonym PS can be communicated externally.

The security token PS can be provided in two different variants:

1. as a digital code in the form of a pseudonym PS; or
2. as a hardware component, e.g. in the form of a USB stick with a corresponding chip for identification or in the form of a security card containing the code, which can be implemented either as a magnetic strip or on the chip, wherein other data media and/or keys are also possible.

Provision is preferably made for the identifier ID to be generated in the registry REG. Alternatively, this can also be executed by a separate entity which is connected to the registry REG via corresponding interfaces.

According to an embodiment of the invention, provision is also made for the security token or pseudonym PS to be generated by the registry REG. In this case a mapping is provided which cross-refers from the person-specific identifier ID to the respective pseudonym PS and vice versa. Likewise, a mapping is provided between the identifier ID and the demographic data DD stored in the registry REG. In other words, the identifier ID can be used to selectively reference or address a data record of demographic data DD in the registry REG.

As shown in FIG. 1 and mentioned above, in the example embodiment the registry REG comprises a security token generator 10 and an identifier generator 11.

An embodiment of the inventive flow sequence of the method for executing a secure access to the security-critical data records is described in greater detail below with reference to FIG. 1.

In FIG. 1, the exchanged messages are labeled by the designations "S1", "S2", "S3" and "S4". In this case the numeral is intended to signify the sequence of the steps in an example embodiment.

The steps labeled "S" designate those messages which are exchanged between data source and registry/repository. The access to the repository REP when executed by the data source Q is a STORE or write access (and therefore the messages exchanged in connection with the data source Q are designated S (for STORE)).

In contrast, the data sink S is so embodied as to read data from the repository (or from the registry); a RETRIEVE command is therefore used. The messages exchanged in connection with the data sink S are accordingly designated by an "R", e.g. "R1", "R2", "R3" and "R4" (see FIG. 1). As in the case of the STORE command, the numeral is intended to signify the sequence of the steps in a preferred embodiment.

The following flow sequence preferably applies when executing a write access.

In a first step S1, the data source Q accesses the registry REG by way of a registration module 22, specifying an identifier ID. The identifier ID can be an identifier that uniquely designates the data within the data source Q. The identifier ID need not necessarily also be an identifier for the data records in registry REG and/or repository REP, since a mapping to the internal identifier (internal to registry and repository) is provided. The identifier ID which is sent from data source Q to registry REG can be a selection of demographic data DD such as patient name, patient date of birth or other patient-related data records, for example.

The identifier is then received and processed by the registry. If the identifier is already an internal identifier, no further mapping functions to the internal identifier are required. Otherwise, if the identifier ID which is sent from the data source Q to the registry REG is therefore only a part of the demographic data and is consequently not embodied to uniquely identify person-specific data (e.g. patient name only), a mapping function is provided in order to generate a system-internal identifier ID from the received part of the demographic data DD. This is performed by the identifier generator 11 of the registry REG. On the basis of the identifier ID that is determined in this way, a pseudonym PS can be generated. This is performed by the security token generator 10 of the registry REG. Provision is advantageously made for a bijective mapping between identifier ID and pseudonym PS in this case. Precisely one identifier can then be associated with precisely one pseudonym.

The following two steps are then executed, the sequence thereof being variable.

A message is sent from the registry REG to the repository REP, comprising the security token PS that has been issued and the associated person-identifying identifier ID to the repository REP, such that the repository REP can use this received data as a mapping rule for subsequent accesses.

Before, after, or concurrently with this step, the pseudonym PS that has been determined is sent to the registration module 22 of the data source Q in step S2. It is important in this case that the pseudonym PS has only temporary validity and expires after a configurable time period. This means that a data access to the repository REP is only possible within the validity period.

In a third step S3, an access to the repository REP is executed by an access module 24 of the data source Q, during which access the allocated pseudonym PS is communicated to the repository.

In this message, concurrently with this message, or in an additional further message (possibly in a different format and/or using a different communication protocol, e.g. via postal devices or mobile radio network), security-critical data SD can then be sent from the access module 24 of the data source Q to the repository REP in step S4. The repository REP then has all of the information required to index the access on the repository REP. For this purpose, the repository REP uses the association from the mapping rule which it received from the registry REG. On the basis of this mapping rule it can uniquely associate the pseudonym PS, which was received in step S3, with an internal person-identifying identifier ID. Using the associated identifier ID, it is possible to index the security-critical data SD that is being accessed.

The RETRIEVE command is described below with reference to FIG. 1.

In a first step R1, a registration inquiry is sent as a message from the registration module 32 of the data sink S to the registry REG. The registration inquiry preferably contains an identifier for the purpose of identifying the data record. This can be an identifier which is used on the data sink S. It is not necessary for said identifier to be used also as an identifier in the registry REG and/or in the repository REP, since a mapping rule is provided according to an embodiment of the invention. This situation also applies to the message which is sent from the data source Q to the registry REG, and is indicated in FIG. 1 in that the message from data source/data sink to registry REG always includes an alternative, namely "ID/DD". This is intended to signify that the identifier being sent does not necessarily have to be allocated by the system. It can be "mapped" onto a system-internal identifier ID by way of the mapping rule.

Following receipt of the message R1, the registry REG can allocate the security token PS to the relevant identifier that has been sent. As explained above in connection with the STORE command, a message is then sent in an optional sequence from the registry REG to the repository REP, thus notifying the repository of the "ID-PS" association.

The associated pseudonym PS (the term pseudonym is used in the context of this description as a synonym for the term security token) is also sent to the registration module 32 of the data sink in step R2.

In a subsequent access phase, the data sink S can then send the received pseudonym PS to the repository REP by means of the access module 34 in step R3.

The repository REP is able to infer the system-internal identifier ID from the received pseudonym PS by virtue of the mapping rule "ID-PS" (received from the registry REG). The security-critical data record SD can be indexed by means of the identifier ID. The data record SD is sent to the access module 34 of the data sink in step R4.

As shown in FIG. 1, none of the exchanged messages contains sensitive data (security-critical data or demographic data) in combination with a person-identifying identifier (e.g. patient name, etc.). This means that even if one of the messages is intercepted, it contains either only the security-critical data (e.g. patient images, findings, etc.) or only the patient-identifying data or parts thereof (e.g. patient name, patient date of birth, etc.). It is not possible to make an association between medical health data and a patient even if a message is intercepted.

The repository REP is embodied to include an index module 42, which is provided for the purpose of indexing the respective security-critical data for access.

Figure 3:
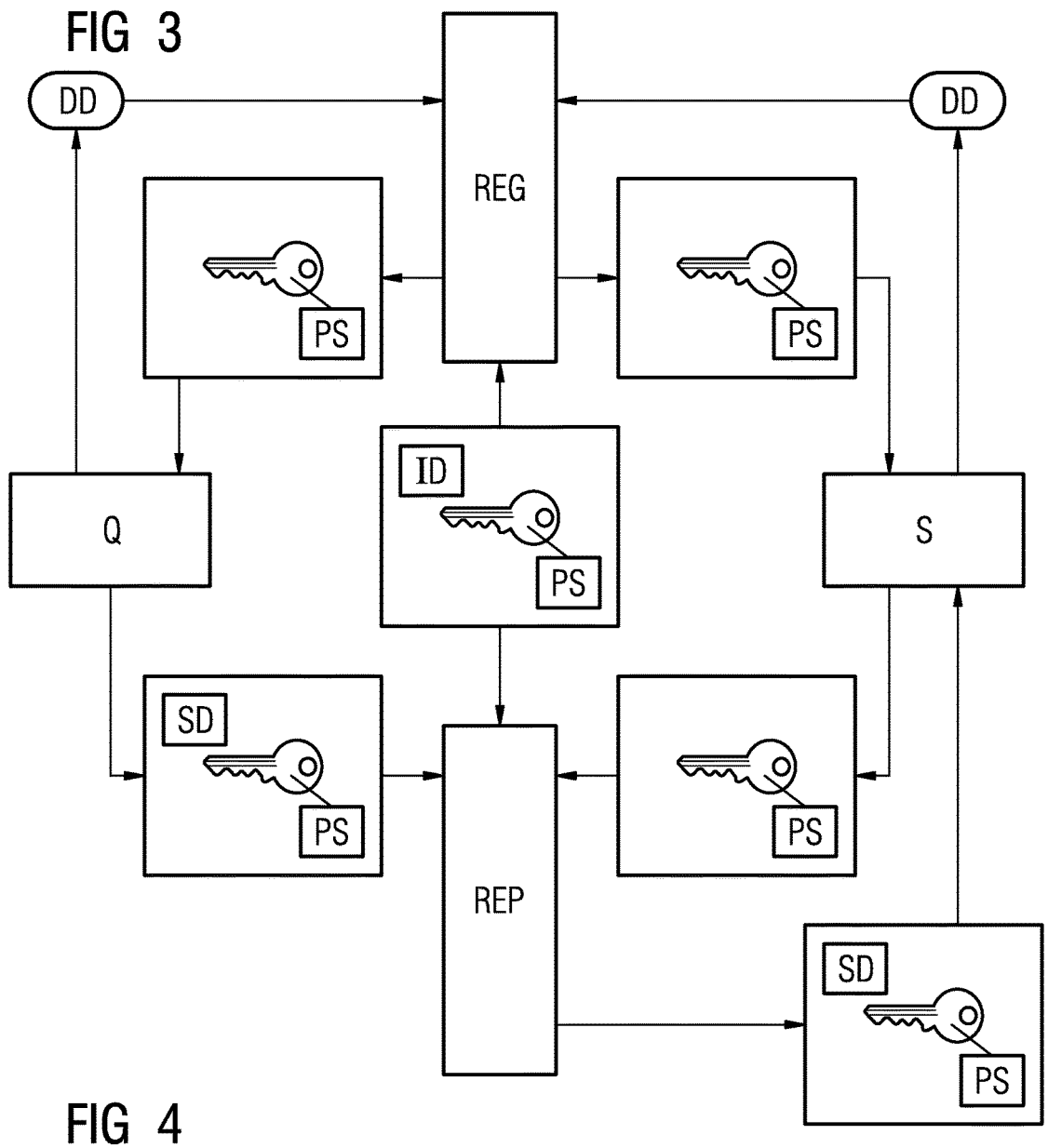
FIG. 3 shows a schematic representation of physical features and messages that are exchanged between the individual entities.

As described above, the security token can be a digitally encoded signal in the form of a pseudonym PS or else a hardware component. An embodiment of the invention is explained below with reference to FIG. 3, in which the security token is a key that has been allocated and is carried on a physical medium such as e.g. a chip card or a chip or an optical signal, for example in the form of a barcode, e.g. a one-dimensional barcode or preferably a 2D barcode in accordance with the data matrix standard (e.g. ISO/IEC 16022:2000 and ISO/IEC TR 24720:2008).

In this embodiment, provision is made for the communication channel on which the security token PS is transferred to be different from the communication channel that is used for the exchange of messages comprising identifier ID, demographic data DD, and security-critical data SD. The demographic data DD, the security-critical data SD and the identifier ID are preferably exchanged via a computer network, e.g. the internet, while the security token PS in this embodiment is transferred by other devices, e.g. postal devices, as a security feature in a physical incarnation, e.g. in the form of a chip card or similar. In this case the security token PS contains a registration profile which is required in order to execute an access to the repository REP. This profile is then compared by the repository REP with the reference profile that was received from the registry REG in a separate message. The message that is sent from the registry REG to the repository REP may also be transferred using different communication protocols and/or networks in this case, e.g. via postal devices or also via the internet as a digital message. If registry REG sends the allocated security token PS to data source Q or repository REP as an analog message, e.g. via postal devices, the receiving entities are provided with a conversion module for automatically transforming the received signal into a digital signal which can then be processed further on the entities.

Figure 4:
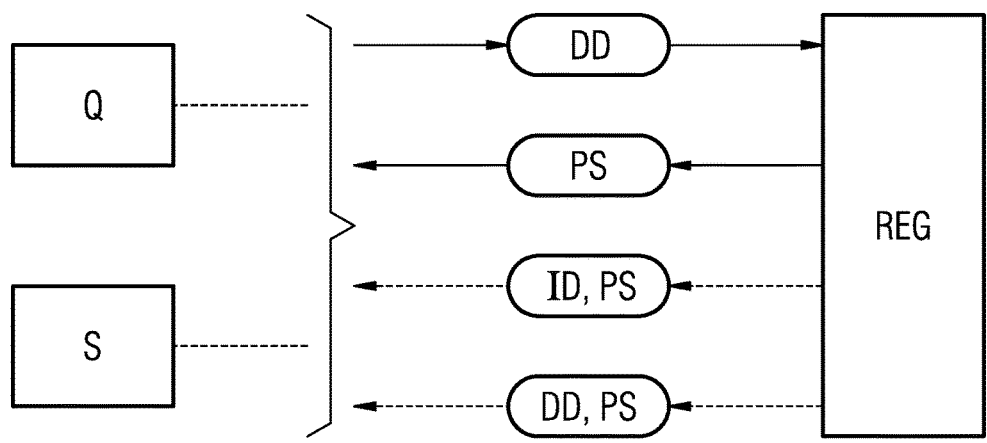
FIG. 4 shows a schematic representation of messages that are exchanged between a registry and a data source/data sink for the purpose of registration.

With reference to FIG. 4, the different ways in which the registry REG can reply to a registration inquiry from the data source Q or the data sink S are described in greater detail. This relates to the messages S2 (for the data source Q) and R2 (for the data sink S).

A security token or pseudonym PS is generated at the registry REG as a reply to a registration inquiry from the inquiring entities (data source Q, data sink S). According to an embodiment of the invention, various options are now provided for forwarding the reply signal to the inquiring entities in step S2 or R2. In a first case, only the pseudonym PS is forwarded. This is indicated in FIG. 4 by the continuous arrow. Alternative options are indicated in FIG. 4 by means of a dotted line. One option consists in transferring a combination message comprising identifier and pseudonym. This may take the form of a (digital) data set or a combination letter sent via postal devices, for example. Alternatively, two combined messages are conceivable here. The identifier relates in this case to a system-internal identifier which is used by registry REG and/or repository REP. A further option consists in receiving the signal from the registration inquiry and sending back a combination message comprising demographic data DD from the inquiry message (transmitted in step S1 or R1) combined with the pseudonym PS that has been allocated.

If solely the allocated pseudonym PS is transferred on its own, and not a combination message, the inquiring entity Q, S has the task of establishing an association between the data from the registration inquiry (S1, R1) and the pseudonym PS that is received. This can be performed via a temporal association or an address function.

Essentially it is provided according to an embodiment of the inventive solution for a registration inquiry to be made to the registry REG in each case before an access to the repository REP (or to security-critical data SD of the repository REP) in order to obtain the pseudonym PS for access to the repository REP. Therefore the access to the repository REP always requires an access to the registry REG first. However, it is also possible for data source Q or data sink S to wish merely to access data which is stored in the registry REG and has a lower security profile. This may include an access to the place of birth for a specific patient, for example. In this case provision is made for the registry REG merely to execute a first mapping function in response to the registration inquiry, wherein the mapping function specifically filters out the relevant data record from the demographic data DD (or part thereof) that was contained in the registration inquiry S1, R1. The data record thus indexed can then be sent back to the inquiring entity as a reply. This also covers instances in which, for example, the data source Q or the data sink S wishes to perform an update on its registration data. The generation of a pseudonym PS and the subsequent steps including the access to the repository REP can then be omitted.

It is therefore provided that not all of the steps of the method of an embodiment need to be executed.

Owing to the asynchronous protocol it is possible for the messages that are exchanged to be independent of one another with regard to the data exchange (e.g. time). As a consequence, the data source Q (like the data sink S) can send messages to the registry REG or the repository REP concurrently, for example.

Provision is preferably made for a configuration phase in which security parameters can be specified for the exchange of data. In this way the validity period for the pseudonym allocation PS can be specified, for example.

Also considered a security precaution in an example embodiment is the fact that every access to the repository REP is subject to a successful registration. Accesses to the repository REP can only be executed by means of a pseudonym PS. "Direct" access to the repository REP using person-identifying data or parts thereof is precluded.

In an example embodiment, the method is provided in the form of a computer-implemented method. In this way it can find application in a distributed environment such that individual steps of the method are executed on different computer-based entities. Likewise, individual executable program parts may be loaded on the relevant computer only, and not be available as executable code.

The computer program or parts thereof may be hard-wired and integrated in the hardware entities, they may be provided as separate add-on modules, or they may be stored on a storage medium.

The registry REG is usually operated as an international supervisory certificate authority, while the repositories REP are operated by different national and/or regional authorities that are registered with the registry REG. The data sources Q and/or data sinks S may take the form of any entities and applications in the context of a health system or other applications. It is also possible for data source Q and data sink S to swap their functions during operation and assume the reverse role respectively. If data source Q or data sink S are radiological systems, for example, they can function alternately as data transmitter/source and data receiver/sink. Their role is therefore not fixed.

According to an example embodiment, the "roles" of data source Q and data sink S can be swapped as mentioned above. Therefore these entities advantageously have the same structure, such that the registration modules 22, 32 correspond in functional terms. The same applies to the access modules 24, 34.

The access system according to an example embodiment of the invention can likewise be limited to a specific type of access only. If it is to be restricted to STORE access only, it consists solely of registry REG, data source Q and repository REP. If it is to be configured for RETRIEVE access only, the system consists solely of registry REG, data sink S and repository REP. The scope of this application also covers parts of the system described above and the individual entities.

According to an example embodiment, operation of the registry REG can be fully automatic. No user interaction is required for the operation of the registry. This makes it possible to reduce both costs and management overhead.

It is also considered an advantage of an embodiment of the inventive solution that the system is scalable inasmuch as individual entities can be added, removed or changed at any time. Therefore data sources Q, data sinks S or further repositories REP can be added even during operation.

It is considered a further advantage that the registration and associated processes are not performed unnecessarily. A registration is only requested and executed on the registry if the data source Q or data sink S is planning to access the repository REP. Consequently, no unnecessary registration data is generated on the registry REG, thereby also avoiding the need to manage such data.

The association of the data with its storage location, and hence the separation of sensitive data which is stored in the registry REG and data that is stored in the repository REP, is preferably performed automatically by another entity. According to an embodiment of the invention, demographic data DD which is also person-related does not contain any health information and is used for administrative and/or identification tasks. It preferably contains the name, the place of birth, the date of birth, the insurer, the employer or other parameters relating to the person concerned.

According to an embodiment of the invention, different variants are provided for generating the security token PS. In a first variant, the pseudonym PS is created as a function of the data from the registration inquiry. In other words, the data identifier ID and/or all data or selected data from the demographic data DD is used as an input for the identifier generator 11 in order to generate the pseudonym PS. Alternatively it is also possible to generate the pseudonym PS independently of the data from the registration inquiry, and to provide a configurable generation rule here for the purpose of generating the security token or pseudonym PS. In this case a hash function can be used on all or a selection of the following parameters:

- a one-to-one global identifier, for example a globally unique number comprising 128 bits as a so-called Global Unique Identifier (GUID);
- a local time, in particular a system time;
- a random number; and/or
- the expiry time for the validity of the pseudonym PS.

As mentioned above, the identifier can also be generated on the registry or alternatively on the inquiring entities such as data source Q or data sink S. In the second alternative, the inquiring entities would immediately use the identifier ID for the registration. Otherwise, the external identifier would have to be "mapped" onto the system-internal identifier ID.

The repository REP is therefore characterized by the provision of two data structures, a static data structure in which a (permanently allocated) association between identifier ID and security-critical data SD is stored, and a dynamic data structure in which an association between (dynamically allocated) pseudonym PS and identifier ID is stored. The repository additionally comprises interfaces for the exchange of data with the other entities. The same naturally applies also to the other computer-based entities.

In summary, the proposal explained in greater detail above can be described as providing a model by which the exchange of sensitive data having different security levels can be performed via the unsecured internet. Security-critical health data SD is stored separately from demographic data DD in this case. Access to the security-critical data SD can only be performed by means of a pseudonym PS following successful registration.

The invention claimed is:

1. A method for secure access to data records in an unsecured network environment, the method comprising:
   providing a central registry and at least one repository separate from the central registry, wherein data is exchanged between the central registry, the at least one repository, at least one of at least one data source and at least one data sink, each of the at least one data source and data sink being registered with the central registry once for data access to the repository, the data records including security-critical data and demographic data of a person, wherein the security-critical data of the person is not communicated between the central registry and the at least one of the at least one data source and the at least one data sink, and person-identifying data is not communicated between the at least one repository and the at least one of the at least one data source and the at least one data sink;
   providing the security-critical data and the demographic data in physically separate devices, by storing the demographic data in the central registry and the security-critical data being accessible in the at least one repository;
   sending a registration inquiry from the at least one of the at least one data source and the at least one data sink to the central registry to obtain a registration in the form of an allocation of a security token for access to a data record associated with a person;
   issuing a temporarily valid security token that is uniquely associated with a person-identifying identifier, in response to the registration inquiry;
   sending a message from the central registry to the at least one repository, the message including the issued security token and the associated person-identifying identifier as a mapping rule;
   communicating using a first access message and a second access message between the at least one repository and the at least one of the at least one data source and the at least one data sink to one of write or access the security-critical data in the at least one repository, the first access message including the security token, the second access message including the security-critical data;
   applying the mapping rule on the at least one repository to derive the person-identifying data record using the security token from the first access message and index the requested data record via the person-identifying identifier; and
   executing the secure access to the indexed data record.

2. The method of claim 1, wherein the security token expires following a configurable time period.

3. The method of claim 1, wherein the association between the security token and the person-identifying identifier is managed by at least one of the central registry and the at least one repository.

4. The method of claim 3, wherein the data records are medical or health-related data records of a patient and the at least one of the at least one data source and the at least one data sink is a medical image storage system.

5. The method of claim 1, wherein the data records are medical or health-related data records of a patient and the at least one of the at least one data source and the at least one data sink is a medical image storage system.

6. The method of claim 1, wherein the security-critical data is not stored directly in the at least one repository and the at least one repository stores an electronic link to access the security-critical data.

7. The method of claim 1, wherein at least one of an asynchronous and synchronous communication protocol is used.

8. The method of claim 1, wherein the security token is at least one of an analog signal, a hardware component and a software component.

9. The method of claim 8, wherein the security token is a barcode.

10. The method of claim 1, wherein the access comprises write accesses to the at least one repository from the data source and read accesses to the repository from the at least one data sink.

11. The method of claim 10, wherein as a reply to an access inquiry comprising the security token of the at least one data sink for the purpose of executing a read access, the at least one repository sends only the requested security-critical data or a combination of security token, or an identification code that is unique to the registration inquiry, and the requested security-critical data to the at least one data sink.

12. The method of claim 1, wherein the at least one repositories, the at least one data source and the at least one data sink are at least one of added, removed and changed during operation.

13. A system for secure access to data records in an unsecured network environment, comprising:
   a central registry including a first memory configured to store demographic data, and a first processor configured to,
      issue a temporarily valid security token in response to a registration inquiry from at least one of at least one data source and at least one data sink, the security token being uniquely associated with a person-identifying identifier, and
      send a message to at least one repository, the message including the issued security token and the associated person-identifying identifier;
   the at least one repository physically separated from the central registry, the at least one repository including a second memory and a second processor configured to store and manage security-critical data; and
   the at least one data source and the at least one data sink, the at least one data source and the at least one data sink including a third processor and a fourth processor, respectively, the third and fourth processors configured to,
      register once with the central registry for data access to the at least one repository,
      send the registration inquiry to the central registry,
      receive the security token as a reply to the registration inquiry, and
      communicate using a first access message and a second access message between the at least one repository and the at least one of the at least one data source and the at least one data sink to one of write or access the security-critical data in the at least one repository, the first access message including the security token, the second access message including the security-critical data,
   wherein the data records include security-critical data and demographic data of a person and wherein the security-critical data of the person is not communicated between the central registry and the at least one of the at least one data source and the at least one data sink, and the person-identifying data is not communicated between the at least one repository and the at least one of the at least one data source and the at least one data sink.

14. A non-transitory computer readable medium comprising computer readable instructions, which when executed by a processor cause the processor to execute the method of claim 1.

15. The method of claim 2, wherein the data records are medical or health-related data records of a patient and the at least one of the at least one data source and the at least one data sink is a medical image storage system.

* * * * *

UNITED STATES PATENT AND TRADEMARK OFFICE
CERTIFICATE OF CORRECTION

PATENT NO. : 9,721,118 B2
APPLICATION NO. : 13/982574
DATED : August 1, 2017
INVENTOR(S) : Georg Heidenreich et al.

It is certified that error appears in the above-identified patent and that said Letters Patent is hereby corrected as shown below:

On the Title Page

Item (73) should read:
(73) Assignee: SIEMENS AKTIENGESELLSCHAFT,
Munich (DE)

Signed and Sealed this
Tenth Day of April, 2018

Andrei Iancu
*Director of the United States Patent and Trademark Office*